United States Patent [19]

Wilk et al.

[11] Patent Number: 5,403,706
[45] Date of Patent: Apr. 4, 1995

[54] CARRIER MATRIX WITH DISSOLVABLY IMPREGNATED REAGENT

[75] Inventors: Hans-Erich Wilk, Lorsch; Dieter Mangold, Maxdorf; Rolf Lerch, Ilvesheim; Joachim Steinbiss, Lorsch, all of Germany

[73] Assignee: Boehringer Mannheim GmbH, Mannheim, Germany

[21] Appl. No.: 383,759

[22] Filed: Jul. 20, 1989

[30] Foreign Application Priority Data

Jul. 30, 1988 [DE] Germany .................. 38 26 055.7

[51] Int. Cl.⁶ .................. C12Q 1/00; G01N 33/53; G01N 33/552; C12N 11/06
[52] U.S. Cl. .................. 435/4; 435/7.1; 435/181; 436/527; 436/531; 530/815; 525/54.1; 525/56; 427/185
[58] Field of Search .................. 435/4, 7, 181, 7.1; 436/527, 531; 530/815; 525/54.1, 56; 427/185, 383, 441

[56] References Cited

U.S. PATENT DOCUMENTS

| 3,992,158 | 11/1976 | Przybylowicz et al. | 435/14 |
| 4,690,907 | 9/1987 | Hibino et al. | 436/514 |
| 4,725,273 | 2/1988 | Kira | 623/1 |
| 4,885,207 | 12/1989 | Johnson et al. | 530/815 |
| 4,950,454 | 8/1990 | Masuda et al. | 422/56 |

*Primary Examiner*—Mindy B. Fleisher
*Attorney, Agent, or Firm*—Felfe & Lynch

[57] ABSTRACT

A carrier matrix of polyvinyl alcohol-coated glass is dissolvably impregnated with reagent. The matrix is manufactured by slurrying glass fibers in an excess of water and polyvinyl alcohol and forming a layer, which is then dried and impregnated with reagent.

10 Claims, 1 Drawing Sheet

CARRIER MATRIX WITH DISSOLVABLY IMPREGNATED REAGENT

BACKGROUND OF THE INVENTION

The present invention is concerned with a carrier matrix dissolvably impregnated with reagent and with a process for the production thereof, as well as with the use thereof.

More particularly, the present invention is concerned with the use of a special carrier matrix for dissolvable impregnation with reagents.

In clinical diagnosis, as well as also in the analysis of foodstuffs, articles of consumption and water, many frequently occurring parameters are determined. For this purpose, detection processes with the use of enzymes or detection processes with the use of immunologically active substances are often carried out. For these determinations to be carried out continually, previously produced test kits are already commercially available which contain all the components necessary for an analysis. In the simplest form, the individual components are present in the form of solutions which are mixed in appropriate amounts with the sample to be investigated. However, many substances, especially biologically active molecules, are not stable in solution and cannot be stored in this form for a comparatively long period of time. In order to avoid this disadvantage, such substances are often stored in dry form and only dissolved immediately before carrying out the analysis in an appropriate liquid and used in the form of a solution. For example, lyophilisates can be so used. However, a disadvantage of lyophilisates is the process for the preparation thereof, which is very laborious and expensive.

It is also known to press substances in solid form into tablets and thus to produce dosage units. However, problems frequently arise when these tablets are pressed too hard because they then only dissolve with difficulty. If, on the other hand, they are not pressed hard enough, the tablets have an insufficient hardness and crumble so that the dosing becomes inexact.

In order to avoid these disadvantages, it has already been suggested to impregnate paper fleece with reagents and then to introduce these paper fleece into the reaction solution during the determination process. For this purpose, the reagent must, on the one hand, adhere very well to the paper fleece in order that the amount which is impregnated on the fleece is not changed due to premature loosening. On the other hand, it is necessary that the applied reagent is eluted quickly and completely when the paper fleece is introduced into the reaction solution. The previously known paper fleece are not satisfactory in these respects since they either do not bind the applied reagent sufficiently well so that, even during storage, a part of the applied reagent is detached or the binding of the reagent is so strong that it cannot be eluted quickly and completely.

In recent years, especially for clinical diagnoses for the investigation of body fluids, for example urine, blood or samples derived from blood, such as serum or plasma, so-called carrier-bound tests have been increasingly used. In the case of these tests, dry reagents are present in or on at least one solid carrier layer which is brought into contact with the sample to be tested. Depending upon the purpose which such a test layer is to fulfill in the carrier-bound test, the reagents can be present in fixed form or in elutable form on the test layer functioning as reagent carrier.

From published European Patent Application No. 0,262,445, there is known, for example, a multi-layer test carrier for the analysis of liquids, especially of body fluids, such as blood and urine, which contains a liquid-absorbing layer which takes up the sample liquid and in which the reagents necessary for the detection reaction are present in different layers separated from one another on different carriers. In order to react the reagents with the components of the sample to be detected exclusively in the liquid-absorbing layer, it is necessary that the reagents, upon contacting the liquid to be investigated, pass completely from the test layer into the liquid-absorbing layer. As appropriate test layers, besides papers impregnated with reagents, there are suggested especially those which contain the reagents embedded in a film of water-soluble material. The film is to consist of a high molecular weight, polymeric material, xanthan being described as preferred. A disadvantage of such test layers is that, when the reagents go into solution, the film-forming material also gets into the sample to be investigated. Under certain circumstances, this can lead to disturbances, for example if the film-forming material interacts with the sample components to be determined. Especially high molecular weight, polymeric, water-soluble materials considerably increase the viscosity of the dissolving liquid, even in low concentrations. The detection reactions then often take place very slowly, being controlled by diffusion. The dissolving of the reagent from the film functioning as the carrier by means of diffusion can be considerably delayed. However, it is often desired that the reagents go into solution very quickly upon contact with a liquid so that the detection reaction takes place very quickly.

SUMMARY OF THE INVENTION

It is an object of the present invention to ensure that the reagents can be dissolved off from the surface of an insoluble carrier. Furthermore, the reagents are to be applied as simply as possible to the appropriate carrier without the use of laborious processes, as when impregnating a carrier with appropriate solutions of the reagents. Therefore, it is an object of the present invention to provide such a carrier matrix dissolvably impregnated with reagent, i.e. a solid material which is water-insoluble under the conditions of use and which, after impregnation, carries the reagent on the surface, which can be stored a long time without the impregnated reagent substantially losing activity and which permits a rapid and complete dissolving off of the reagent with maintenance of its activity.

In particular, it is an object of the present invention to provide such a carrier matrix dissolvably impregnated with reagent which can be used in test devices and processes for the determination of sample components.

An object of the present invention is especially to provide a carrier matrix which can be used for the dissolvable impregnation with reagents.

Surprisingly, we have found that a carrier matrix of polyvinyl alcohol (PVA)-coated glass impregnated with reagent fulfills this task.

Such a carrier matrix leads to such a stabilisation of the impregnated reagents that, even after comparatively long storage and even after storage at elevated temperature, no substantial activity loss occurs. Furthermore, the PVA-coated glass carries reagents impregnated thereon in such a manner that these, upon contact with a liquid and especially with a sample liquid to be investigated, are completely dissolved off very quickly, possibly within a few seconds. After dissolving off of the reagent from the impregnated carrier matrix according to the present invention, the reagent possesses essentially the same properties as before the impregnation on to the matrix.

In order to achieve these advantageous properties, the carrier matrix must comprise two components. The first is a glass which, in principle, can be present in any desired form and composition.

The second component is polyvinyl alcohol, with which the glass is coated. Polyvinyl alcohol is usually produced from polyvinyl acetate by saponification in which case, depending upon the desired properties of the product, a complete or partial saponification is carried out. For the use according to the present invention, there can be used not only a completely but also a partly saponified product. Polyvinyl alcohols, which are commercially available in large amounts, differ especially by their average molecular weight, which is normally from about 10,000 to 100,000 and, in some special cases, can also have substantially higher values, as well as by the residual content of acetyl radicals. The low molecular weight compounds, which contain about 5 to 15% and especially about 10% of acetyl radicals, are the most easily soluble in water, whereas high molecular weight and/or higher acetyl-containing products are less soluble in water. The Interaction of the polyvinyl alcohol chains with one another also has an influence on the solubility. Due to a parallel positioning of the polymer chains in certain regions, "crystalline" zones arise, the orientation tendency being the greater, the more regularly the chains are constructed and the smaller is the proportion of the acetyl radicals which counter an orientation the most strongly. Therefore, in the case of a degree of saponification of 97 to 100 mol %, i.e. in the case of a degree of acetylation of 3 to 0 mol %, the "crystallinity" increases especially strongly, whereas, on the other hand, the cold water solubility decreases strongly.

Furthermore, the water solubility can be reduced by after-treatment with aldehydes (acetalisation) or by other chemical changes of the alcohol groups. According to the present invention, there are preferably used those polyvinyl alcohols with a very low cold water solubility. At a temperature of 20° C., the products are to dissolve in water only slowly or not at all. However, at temperatures of 50°–100° C. and especially at temperatures above 60° C., a solubility in water is not disadvantageous.

In the carrier matrix according to the present invention impregnated with reagent, the glass is so covered with a PVA layer that the whole glass surface is covered. For optimum storage and reagent dissolving properties, the glass is coated with about 0.5 to 20% by weight and preferably with 2.1–10% by weight of PVA.

According to the present invention, the PVA-coated glass can, as carrier matrix, be present in any desired form. In order to make available the greatest possible surface, it can be advantageous to make the carrier matrix in the form of fibres. For many purposes, it is sufficient to use the matrix in the form of fibre skeins in which the individual fibres are completely irregularly arranged. However, it is often desired to have planar reagent carriers which are in the form of sheets or layers. In such cases, it is quite especially preferred when the carrier matrix is a fleece.

A glass coated with PVA, especially one in fibre form and quite especially a glass fibre fleece coated with PVA, is very appropriate for impregnation with reagents. From published European Patent Application No. 0,239,002 (U.S. Pat. No. 4,788,152) are already known PVA-coated glass fibre fleece, such as have been previously described. However, they there merely serve for the transport of serum and plasma, as well as possibly for the separation of erythrocytes from blood. An impregnation with reagents is not discussed in this European Application. Therefore, it was not to have been expected that, by impregnation of glass coated with PVA with reagents, reagent carriers are obtained which solve so well the problem forming the basis of the present invention.

When proteins are impregnated on to a carrier matrix according to the present invention, upon contact with a liquid and especially with a sample liquid to be investigated, they are, as a rule, dissolved very quickly and completely and thereby not denatured, i.e. after the dissolving off procedure from the matrix, they are present with substantially the same biological activity as before the impregnation of the matrix with the corresponding protein solution.

Quite especially preferred reagents impregnated onto the carrier matrix are those used for enzymatic determinations, such as enzymes, and those used for immunological detection reactions, such as antigens, antibodies and/or fragments thereof, as well as conjugates of immunologically active substances with labelling substances, for example enzymes. In the same way, other binding components can also be dissolvably impregnated onto the matrix, for example biotin/avidin or streptavidin, protein A/immunoglobulin G or concanavalin A/mannose, as well as conjugates of these substances with enzymes or antibodies or antibody fragments.

Outstanding results with regard to rapidity and completeness of the dissolving again of reagents from the matrix, as well as with regard to the storage stability of the matrix, are obtained with enzymes, especially with $\beta$-galactosidase, and with conjugates of immunologically active substances and labelling substances, especially with conjugates of IgG molecules with $\beta$-galactosidase.

Besides the actual "active" components of the reagent, for example enzymatically and/or biologically active proteins, the reagent can also contain further substances. In particular, the reagent can also contain materials which are appropriate or necessary for maintaining the activity or avoiding the deactivation of the reagent in solution. For this purpose, there are to be understood especially buffer substances for the maintenance of a definite pH value in solution, detergents, salts or particular protective substances, such as albumin or saccharose.

The reagent concentration on the carrier matrix can be varied in wide limits without this having a substantial influence on the rapidity and completeness of the dissolving off of the reagent. A natural upper limit of the concentration is reached when the reagent no longer adheres firmly to the surface of the PVA-coated glass and, even before use, comes off even in a dry state.

The production of a carrier matrix impregnated with reagent takes place fundamentally by first coating glass with PVA,, impregnating the coated glass with reagent and subsequently possibly drying the impregnated matrix.

Especially for the production of a fleece, an appropriate glass fibre fleece previously prepared is subsequently treated with a solution of polyvinyl alcohol in water or an appropriate organic solvent and subsequently dried. On the basis of the preferred solubility behaviour and of the melting point of PVA, such a treatment of the glass fibre fleece should be carried out at a temperature above 60° C. and preferably at 90° to 140° C.

A PVA-coated glass fibre fleece is preferably so prepared that, already in the case of the preparation of the glass fibre fleece, polyvinyl alcohol is added in solid form and especially preferably in fibre form to the glass fibres.

PVA-coated glass fibre fleece for the matrices are quite especially preferably produced by suspending dry glass fibres, which have an average diameter of 0.1–20 μm. and a length of 0.1–5 mm., in a very large excess of water and thereby singled out, the "pulp" thus obtained then being formed into thin layers analogously to the processes usual in paper production and with the help of the machines usual for this purpose and dried. Polyvinyl alcohol powder or fibres added to the pulp are divided up uniformly in the mass in the slurrying of the glass fibres and, in the subsequent production of the fleece, are dissolved or melted to such an extent that, subsequent to the drying of the fleece, they form a complete and uniform coating on the glass fibres. A glass fibre fleece coated in such a way is, as far as concerns the absorbency and the transport of water or aqueous solutions through this fleece, not impaired in comparison with an uncoated glass fibre fleece.

Since the polyvinyl alcohol covers over the glass fibres relatively uniformly when it is applied as above, even small amounts, especially about 0.5 to 20% by weight and preferably 1 to 10% by weight, suffice to completely cover the fibres with a PVA mantle. Proportions of above 20% by weight would admittedly not be harmful FOR the intended effect but, for process-technical reasons, are often not desirable since, for example, glass fibre fleece with a high PVA content are very rigid.

For the impregnation of the carrier matrix with reagent, this is preferably impregnated with a solution of the reagent, the impregnation solution thereby being applied to the carrier matrix or the carrier matrix being dipped into the impregnation solution. In order to achieve an impregnation of the carrier matrix which is as homogeneous as possible, the latter embodiment is preferred.

The solvent used can be any liquid which dissolves the reagent sufficiently well, does not negatively influence the properties of the reagent and which, after impregnation of the carrier matrix with the reagent, can again be removed to such an extent that properties of dissolving off again and activity of the reagent are not impaired. In the case of enzymatically and/or immunologically active substances, the solvent of choice is water.

After the impregnation procedure, there follows a drying step if the solvent of the reagent has to be separately removed. In the case of using water as solvent, this is frequently the case. Depending upon the nature and composition of the reagent, it must thereby be decided at which temperature the drying procedure has to be carried out and how long it is to take. Especially in the case of reagents with enzymatically and/or immunologically active substances, the temperatures should not exceed about 70° C. and the drying period should not be longer than about 1 hour.

The carrier matrix impregnated with reagent can be used everywhere where, in a liquid, a component material is to be reacted with reagents. In particular and especially advantageously, it can be used where reagents are to be added to a liquid in an easily handled and pre-dosed way, the activity of which has not been impaired by storage. The use of the carrier matrix dissolvably impregnated with reagent offers quite special advantages in test devices and processes for he determination of sample component materials insofar as these are present in a liquid. The matrix is especially outstandingly appropriate for use as reagent carrier in carrier-bound tests for the enzymatic and/or immunological determination of sample component materials.

The present invention is especially appropriate for use in a test carrier for carrying out immunological determinations since the rapid and complete elutability of reagents, especially of immunologically and/or enzymatically active substances, for example antibody-enzyme conjugates, from carrier matrices is there very important.

DETAILED DESCRIBED OF THE PREFERRED EMBODIMENT

Figure 1:
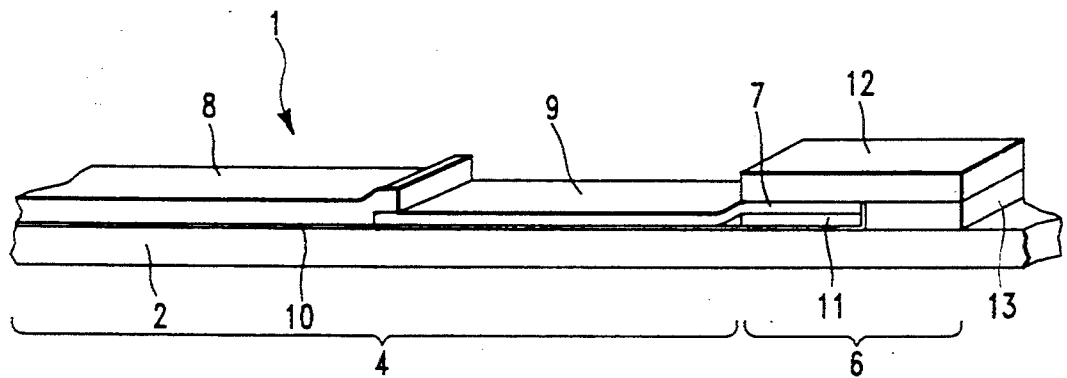
FIG. 1 is a perspective of a test device containing the inventive carrier matrix.

The illustrated test carrier 1 has a base layer 2 on which are fixed the other test layers. In its longitudinal direction, the test carrier can be subdivided into a sample application region 4 and into an evaluation region 6. In the sample application region 4, a conjugate layer 8 and a liquid transport layer 9 are fixed next to one another on the base layer 2 with the help of a melt adhesive 10. The layer 8 slightly overlaps the subsequent layer 9 in order to ensure a fluid contact between them which is as good as possible. The layers 8 and 9 form a liquid transport path which extends from the sample application and pre-reaction region 4 into the evaluation region 6.

In the illustrated example, the sample is applied to the conjugate layer 8, this layer thereby simultaneously serving the purpose of carrying out a first reaction step. The sample application region 4 serves, at the same time, as a pre-reaction region.

In the evaluation region 6 are to be seen on the base layer 2, over one another, a colour-forming layer 11, a cover layer 7 and a holding-down layer 12, this holding-down layer 12 consisting of a comparatively stiff synthetic resin foil. It is so fixed with the help of a melt adhesive strip 13 of correspondingly great layer thickness on to the base layer 2 that it runs parallel to it at a distance which corresponds approximately to the total thickness of colour-forming layer 11 and covering layer 7. The holding-down layer 12 has a sufficient stiffness in order to press together the layers present between it and the base layer 2 in such a manner that a good fluid contact is ensured between them.

In the case of the illustrated preferred embodiment, no further absorbent layers are provided beside the colour-forming layer on its side facing away from the sample application region 4 in the longitudinal direction of the base layer 2 (thus in FIG. 1 to the right of the 5 colour-forming layer 11). Thus, the colour-forming layer 11 is in fluid contact with the last part of the liquid transport path 8, 9, 7 in the liquid transport direction.

In the illustrated preferred embodiment, the colour-forming layer 11 consists of a carrier foil and a retardedly soluble film layer present thereon, which contains a colour-forming reagent.

The test carrier illustrated in the Figure is especially suitable for immunological determinations. Such determinations use highly specific binding reactions between different species which can be designated as binding components. Immunological binding components are especially antibodies on the one hand, as well as antigens or haptens on the other hand.

For the case in which an antigen AG contained in a sample is to be determined as analyte, the following course of the test is, for example, typical.

The sample is applied to the conjugate layer 8 which contains a soluble conjugate ABE of an antibody AB, specifically bindable with the AG, with an enzyme E. Complexes AG-ABE are formed by the specific binding reaction.

Excess ABE passes, together with the AG-ABE complexes, into the liquid transport layer 9 which contains an antigen AGF in Carrier-fixed form. The AGF is identical to the sample antigen or analogous to this, i.e. specifically bindable with the antibody of the ABE contained in the conjugate layer 8.

On the basis of the specific binding reaction, the excess free ABE is now carrier-fixed with the antigen fixed in the layer 9. For the function, it is important that the coating thickness of the fixed antigen AGF on the layer 9 is sufficiently high to ensure that practically the whole of the excess conjugate ABE is bound thereon. Therefore, the layer 9 can also be referred to as a "fixing layer". Only the free AG-ABE complexes pass into the evaluation zone 6. The amount of the AG-ABE complexes entering into the evaluation zone 6 (and thus the amount of the labelling enzyme E) thereby correspond to the amount of the analyte AG.

The sample liquid with the AG-ABE complexes flow further into the cover layer 7 and fills this completely, essentially before the colour-forming reaction with the colour-forming reagent begins in the layer 11. The delayed commencement of the colour-forming reaction is, as described above, especially achieved in that the layer 11 dissolves retardedly.

The cover layer 7 tan be produced with the fixing layer 9 in one piece, i.e. both layers consist of a strip of the same layer material. This is preferred but not necessary. The cover layer 7 could also be a separate layer which is in fluid contact in any way with the liquid transport path 8, 9.

The liquid penetrates vertically to the layer surface into the colour-forming layer 11. The colour-forming layer 11 contains a substrate for the enzyme E. Depending upon the enzyme concentration, a colour change takes place which is a measure for the concentration of the analyte.

The visual or apparatus evaluation of the colour change can take place from the side of the base layer or of the cover layer. Depending upon the type of embodiment, for this purpose the base or the cover and holding-down layer must have properties such that the colour change in the colour-forming layer can be ascertained therethrough.

The impregnated carrier matrix according to the present invention has proved to be very useful as conjugate layer 8. Especially in its embodiment as PVA-coated glass fibre fleece which is impregnated with an antibody-enzyme conjugate, it ensures the rapid and complete elutability of the ABE. This is very important since the sample liquid is sucked in only a few seconds through the conjugate layer 8 into the fixing layer 9 and, for the above-described immunological method of determination, it is important that the antibody-enzyme conjugate ABE is completely eluted.

The manner of functioning of the test carrier was described above by way of example for the case in which an antigen is to be determined. An analogous course of the test is also possible for the determination of an antibody, in which case an antigen conjugate would then have to be used in the layer 8 and a carrier-fixed analogous antibody in the layer 9.

Apart from the particularities of the present invention, the described immunological course of the test is similar to that described in published Federal Republic of Germany Patent Application No. 36 38 654. Therefore, supplementary reference is made to this publication.

The above-described test device is especially appropriate as a detection unit for a test kit for the determination of an analyte in faeces, as is described in Federal Republic of Germany Patent Application P 37 16 891. This test kit has a sample collection unit in which a liquid which contains the analyte is obtained from faecal samples by elution with the help of an elution agent. The so obtained sample liquid can advantageously be investigated with a test device as has been previously described.

EXAMPLE 1

Production of a Carrier Matrix 1 kg. of glass fibres Type 108 E (John Mansville, Denver/USA) and 0.05 kg. polyvinyl alcohol fibres Type Kuralon VPB 105-2 (Rohtext Textil GmbH, Mönchengladbach, Federal Republic of Germany (FRG)) were suspended in 1000 liter of distilled water. For the production of the fleece, there was used a sloping sieve machine (VOID, Heidenheim, FRG). For the sheet formation, the suspension was pumped on to a sloping sieve. While the liquid flowed off or was sucked off by vacuum, the fibres orientated on the sieve surface and were dried as fleece over drying cylinders, drying taking place at 125° C. until an end moisture of 0.5 to 1.5% by weight had been achieved. The Kuralon thereby melted and deposited as a film on the glass surface. The sucking off and transport speed were so chosen that a material resulted with a weight per unit surface area of 30 g./m$^2$ and a thickness of 0.25 mm.

EXAMPLE 2

Stability of Impregnated Reagent

Carriers were produced of paper (Type 4210, Kalff, FRG), of multifilar polyester fabric (PE 14/100, Schweizer Seidengazefabrik, Thai, Switzerland) and of PVA-coated glass from Example 1 impregnated with reagent. For this purpose, 6×6 mm. sized pieces of these materials were impregnated in each case with 10 μl. of a solution which contained the following components: 10 mmol/liter HEPES, 25 mmol/liter sodium chloride, 1 mmol/liter magnesium aspartate, 2% saccharose, 0.5% crotein C and β-galactosidase, the whole solution having a pH of 7.25.

Immediately after the impregnation, the fleece were dried for 30 minutes at 35° C. in a circulating air drying cabinet and investigated after cooling to ambient temperature, as well as after different stressings.

The β-galactosidase activity was determined after total elution (washing three times with, in each case, 50 μl. of the above-mentioned buffer) in a centrifugal photometer with 50 μl. of the eluate after the addition of 5 mmol/liter chlorophenol red β-D-galactoside (prepared according to published European Patent Specification No. 0 146 866). The measurement values given in the following Table 1 were obtained:

TABLE 1

| | β-galactosidase activity in milli-extinction units (mE) | | |
|---|---|---|---|
| | immediately after impregnation and drying | after 1 week at 45° C. | after 3 weeks at 45° C. |
| paper fleece | 1970 | 1700 | 1510 |
| PE 14/100 | 680 | 618 | 512 |
| PVA-coated glass fibre fleece | 1231 | 1156 | 1216 |

Whereas for the carrier matrix according to the present invention, practically no activity loss was ascertainable even after 3 weeks at 45° C., in the case of impregnated paper fleece and in the case of impregnated polyester fabric, the enzyme activity decreased by more than 20%.

In the case of the use of antibody-enzyme conjugates on PVA-coated glass fibre fleece, the immunological activity also remained unchanged

EXAMPLE 3

Elutability of the Reagent from Reagent-Impregnated Carrier Matrices

Figure 2:
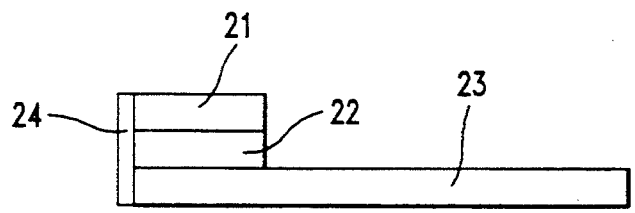
FIG. 2 is an elevation view of an alternative test device containing the invention test matrix.

The elutability of a reagent from correspondingly impregnated reagent carriers was measured after application of a serum sample to a test device according to FIG. 2 of the accompanying drawings.

In FIG. 2, 21 indicates an application zone, 22 a reagent-impregnated carrier matrix and 23 an absorbent fleece, 21, 22 and 23 being held together by a melt adhesive strip 24.

The application zone consisted of a 6×6 mm. glass fibre fleece (Type 108, Binzer, FRG) with a weight per unit surface area of 60 g./m². The absorbent fleece (17×6 mm.) consisted of the same material as the application zone but had a weight per unit surface area of 30 g./m². 22 (6×6 min.) consisted in case a) of a carrier matrix produced according to Example 1,
in case b) of a paper (Type 4210, Kalff, FRG),
in case c) of a nylon fabric (nylon 20 HC, Schweizer Seidengazefabrik, Thal, Switzerland), and
in case d) of a polyester fabric (PE2F777, Schweizer Seidengazefabrik, Thal, Switzerland)
which, in each case, had been impregnated with a solution of 10 mmol/liter HEPES, 25 mmol/liter sodium chloride, 1 mmol/liter magnesium aspartate, 2% saccharose, 0.5% crotein C and a conjugate of polyclonal sheep anti-human serum albumin antibodies with β-D-galactosidase (IgG<hSA>-β-D-galactosidase) with a pH of 7.25. The thickness of the layers 21, 22 and 23 was in each case, about 0.25 mm.

For the measurement of the elutability of the reagent impregnated into 22, 64 μl. of serum (PNU, Boehringer Mannheim GmbH, Mannheim, FRG) were applied to 21. In each of cases a)–d), the absorbent fleece was already filled with liquid after about 25 seconds. At this time, 23 was removed from the test device by means of tweezers and centrifuged out (Eppendorff laboratory centrifuge, 30 seconds at 10,000 r.p.m.). The enzyme activity in the so obtained eluate was determined photometrically after addition of 5 mmol/liter of chlorophenol red β-D-galactoside (prepared according to published European Patent Specification No. 0,146,866).

There were again found the percentage proportions of the enzyme activity originally impregnated on to the carrier matrix given in Table 2.

TABLE 2

| | enzyme activity found again in % |
|---|---|
| PVA-coated glass fibre fleece | 106 |
| paper | 47 |
| nylon fabric | 83 |
| polyester fabric | 80 |

The reagent impregnated on to PVA-coated glass fibre fleece showed, not only with distance, the best finding again rate. The reagent was, furthermore, also eluted quantitatively.

EXAMPLE 4.

A test carrier according to FIG. 1 was produced as follows:

a) Conjugate layer 8

A PVA-coated glass fibre fleece according to Example 1 was impregnated with a solution of IgG<hSA>β-D-galactosidase conjugate in 10 mmol/liter HEPES, 25 mmol/liter sodium chloride, 1 mmol/liter magnesium aspartate, 2% saccharose and 0.5% crotein C with a pH of 7.25 and dried.

The test layer size on the test carrier was 20×6 mm. The conjugate layer contained 200 mU β-D-galactosidase activity.

b) Fixing layer 9 and cover layer 7 hSA was covalently fixed on to a membrane of hydrophilic polyvinylidene difluoride (PVDF) of Millipore (Bedford, USA) which is marketed under the Trade Mark Immobilon AV. The surface concentration was adjusted, via the concentration in the buffer used for the impregnation procedure, to 20 μg. hSA/cm². The layer size was 20×6 mm.

c) Signal-forming layer 11

A film-forming coating mass was produced on the basis of 0.6% Ketrol F of Kelco, Hamburg, FRG, with the addition of 2.5% methylcellulose 15 of Serva, Heidelberg, FRG. It contained 12 mM chlorophenol red β-galactoside (CPRG) and was buffered in HEPES. The coating mass was coated in a film layer thickness of 200 μm. on to a 100 μm. thick carrier foil of Pokalon of Lonza, Weil/Rhein, FRG. The layer size was 6×6 mm.

d) Holding-down layer 12

This consisted of a 140 μm. thick Pokalon foil.

As base layer, there was used a polyester film "Melinex" of ICI, Frankfurt, FRG. The adhesion of the components took place with the melt adhesive Dynapol S 1358 of Dynamid Nobel, Troisdorf, FRG.

In the case of the application of a liquid human serum albumin (hSA)-containing sample to the conjugate layer 8, a colour change from yellow to red could be observed in the signal-forming layer 11 after a few minutes.

Figure 3:
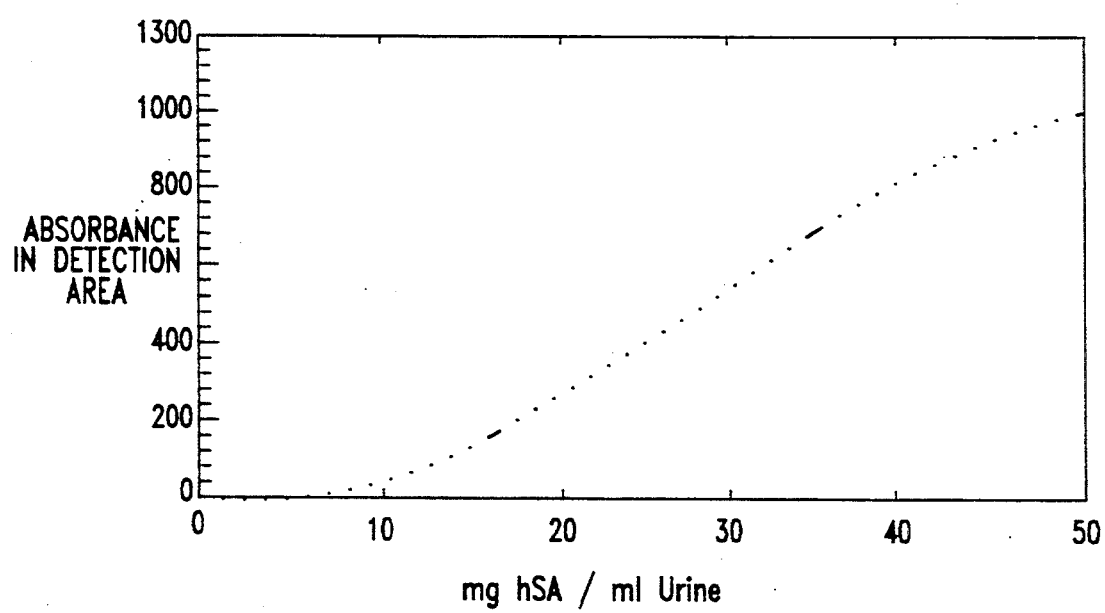
FIG. 3 is a calibration curve obtained with a test device containing the inventive carrier matrix.

By measurement of samples of known hSA content, there was obtained the calibration curve illustrated in FIG. 3 of the accompanying drawings.

We claim:

1. Process for the production of a carrier matrix of polyvinyl alcohol-coated glass, wherein glass fibres are slurried in an excess of water with the addition of polyvinyl alcohol to form a slurry, a layer is formed with said slurry and dried at elevated temperature and the layer is impregnated with an aqueous protein solution.

2. Process for the production of a carrier matrix according to claim 1, wherein said aqueous protein solution is dried.

3. Carrier matrix impregnated with protein which is soluble in a sample liquid, said carrier matrix being dry and consisting of glass and polyvinyl alcohol completely coating said glass, said polyvinyl alcohol being at least substantially insoluble in water at temperatures below 20° C., said protein being soluble in said liquid without denaturation.

4. Carrier matrix as in claim 3 wherein said protein is soluble in water.

5. Carrier matrix according to claim 3, wherein the glass is present in fibre form.

6. Carrier matrix according to claim 2, wherein the glass fibres are worked up as fleece.

7. Carrier matrix according to claim 3, wherein the glass is coated with 0.5 to 20% by weight of polyvinyl alcohol.

8. Carrier matrix according to claim 7, wherein the glass is coated with 1 to 10% by weight of polyvinyl alcohol.

9. Carrier materix according to claim 3, wherein the reagent contains $\beta$-galactosidase or conjugates of antibodies with $\beta$-galactosidase.

10. Process for the production of a carrier matrix of polyvinyl alcohol coated glass impregnated with protein, said process comprising the steps of
providing a glass carrier matrix,
completely coating said glass with polyvinyl alcohol which is at least substantially insoluble in water at temperatures below 20° C., thereby forming a coated glass,
dissolvably impregnating said coated glass with an aqueous protein solution, and
drying said aqueous protein solution.

* * * * *

UNITED STATES PATENT AND TRADEMARK OFFICE
CERTIFICATE OF CORRECTION

PATENT NO. : 5,403,706
DATED : April 4, 1995
INVENTOR(S) : Hans-Erich Wilk, et al It is certified that error appears in the above-indentified patent and that said Letters Patent is hereby corrected as shown below:

In column 3, lines 30-31, change "Interaction" to -- interaction --, and run the text into the preceding paragraph.

In column 3, line 58, change "2.1" to -- 1 --.

In column 4, line 68, after "PVA" delete the second --,--.

In column 6, line 13, change "he" to -- the --.

In column 6, line 32, change "invention" to -- inventive --.

In column 6, line 35, change "DESCRIBED" to -- DESCRIPTION --.

In column 7, line 30, change "Carrier" to -- carrier --.

In column 7, line 53, change "tan" to -- can --.

In column 8, line 64, change "Thai" to -- Thal --.

In column 9, line 36, after "unchanged" add --.--.

In column 9, line 49, before "application" delete the -- ----.

UNITED STATES PATENT AND TRADEMARK OFFICE
CERTIFICATE OF CORRECTION

PATENT NO. : 5,403,706
DATED : April 4, 1995
INVENTOR(S) : Hans-Erich Wilk, et al It is certified that error appears in the above-indentified patent and that said Letters Patent is hereby corrected as shown below:

In column 9, line 54, change "min." to -- mm. --.

Signed and Sealed this

Twenty-third Day of November, 1999

Attest:

Q. TODD DICKINSON

Attesting Officer

Acting Commissioner of Patents and Trademarks